United States Patent [19]

Hill

[11] Patent Number: 5,752,280
[45] Date of Patent: May 19, 1998

[54] EYE PROTECTION DEVICE FOR HEADGEAR

[75] Inventor: Joe D. Hill, Tucson, Ariz.

[73] Assignee: Itech Sport Products, Inc., Quebec, Canada

[21] Appl. No.: 713,014

[22] Filed: Sep. 12, 1996

Related U.S. Application Data

[63] Continuation-in-part of Ser. No. 505,763, Jul. 21, 1995, abandoned, which is a continuation-in-part of Ser. No. 166,018, Dec. 13, 1993, abandoned.

[51] Int. Cl.⁶ .......................................................... A61F 9/02
[52] U.S. Cl. ................................................ 2/453; 351/155
[58] Field of Search ................................. 2/453, 12, 10, 2/6.3, 6.7, 209.13, 424; 351/155, 158

[56] References Cited

U.S. PATENT DOCUMENTS

| | | | |
|---|---|---|---|
| 2,245,990 | 6/1941 | Loud | 2/453 |
| 2,588,553 | 3/1952 | McWethy | 2/453 X |
| 2,700,158 | 1/1955 | Larsen | 2/453 X |
| 4,541,125 | 9/1985 | Phillips | 2/453 X |
| 5,239,703 | 8/1993 | Nordin et al. | 2/10 |

Primary Examiner—Peter Nerbun
Attorney, Agent, or Firm—Marvin S. Towsend

[57] ABSTRACT

An eyeshield removably attached to a headgear. The eyeshield manually rotates from a normal viewing position to an out of viewing position above the forehead by means of two sets of pivotal arms attached to a unique bistable tensioning pivotal mechanism. This mechanism applies tension to keep the eyeshield held firmly in place in the normal viewing position, and when the eyeshield is manually lifted toward the out of viewing position above the forehead, tension is applied in the reverse direction to keep the eyeshield held firmly in the out of viewing position. The position of the eyeshield may also be adjusted with respect to the face of the user.

40 Claims, 10 Drawing Sheets

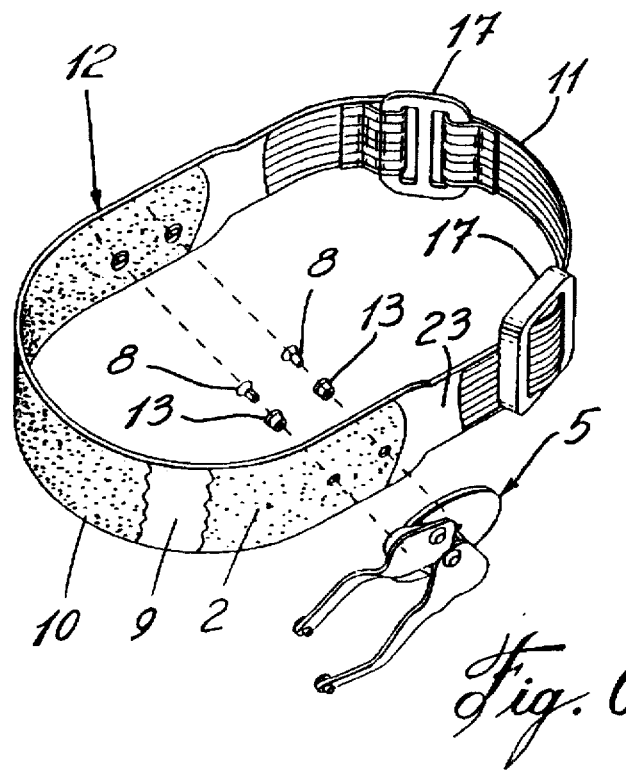
Fig. 6
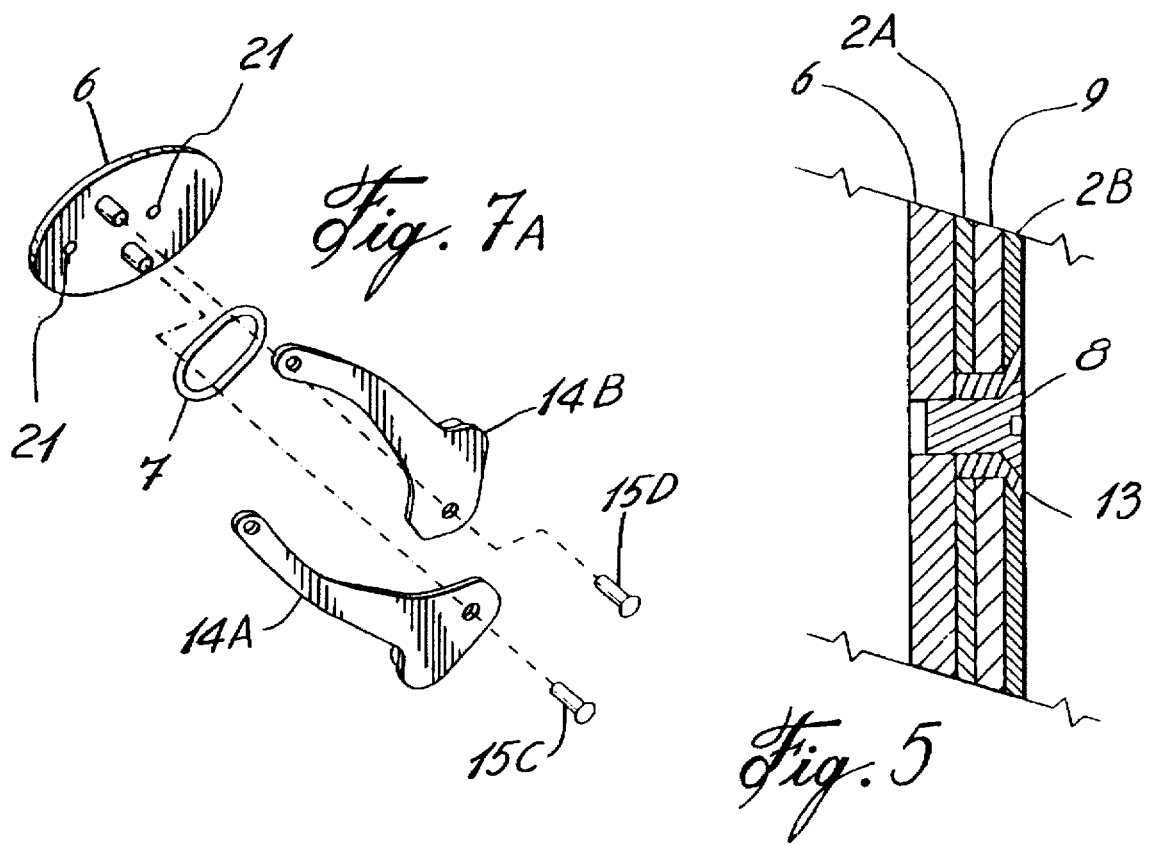
Fig. 7A
Fig. 5

EYE PROTECTION DEVICE FOR HEADGEAR

CROSS-REFERENCE TO RELATED APPLICATION

This application is a continuation-in-part of an earlier filed continuation-in-part U.S. application Ser. No. 08/505, 763, filed on Jul. 21, 1995, now abandoned, which is a continuation-in-part of U.S. application Ser. No. 08/166, 018, filed Dec. 13, 1993, now abandoned.

TECHNICAL FIELD

This invention relates to an eye protection device for securement to a headgear and capable of being retained at a position of use in front of the wearer's eyes and a different position of non-use.

BACKGROUND ART

All outdoor sports participants have to contend with one or more of the three elements that affect a participant's vision during outdoor competition: unfiltered sunlight, perspiration in the eyes, and foreign objects invading the eyes. To try to solve these problems, athletes have had to wear sweatbands and protection glasses.

Sweatbands alone have been used satisfactorily for many years to keep perspiration originating at the top of the head from running into the wearer's eyes.

Normal sunglasses have also been used for many years, and do remain in place during sedate activities such as sitting and walking, but are unable to remain in place during vigorous activities such as basketball, volleyball, racquetball or tennis. During these activities, sunglasses have to be modified in a way that conflicts with their original intended use by placing heavy elastic bands to the ear pieces. These bands expand against the back of the head to apply uncomfortable stresses to the bridge of the nose, the temples and the ears themselves, eventually causing fatigue and pain.

The challenge is to design the glasses to attach to the sweatband in a manner so that: a) a tension device will keep the glasses comfortably in place even during rigorous physical activities, b) the glasses can be quickly and easily rotated out of the line of sight so perspiration can be wiped from the area of the eyes, and then be quickly and easily rotated back into the line of sight, even during the physical activity, and c) providing an eyeshield having improved adjustable features to protect the eyes.

With regard to using tension devices to hold the glasses in place, the prior attempt of U.S. Pat. No. 4,885,808 to Carpenter, issued Dec. 12, 1989, is indicative of the simple flip up approach of using a coiled spring tension device to hold the sunglasses in place. This arrangement also allows the sunglasses to be rotated into and out of the line of sight of the wearer. However, this design is too fragile because of the single tiny flip up mechanism used to attach the eye pieces to the headband. This one fragile attach point would allow even the smallest of impacts experienced during a sports activity to drive the eye pieces into the wearer's eyes and face, posing an unacceptable risk of damage to the eyes and face.

With regard to the ability to quickly and easily rotate the glasses into and out of the line of sight of the wearer, reference is made to U.S. Pat. No. 4,616,367 to Jean, issued October 1986, U.S. Pat. No. 4,712,254 to Daigle, issued December 1987, and U.S. Pat. No. 4,811,430 to Janusz, issued March 1989, as being indicative of the approaches used to hide the eyepieces in a headband to remove them from the line of sight of the wearer. This approach is not only cumbersome and time consuming for the hands to operate, but more importantly, it drastically limits the size and shape of the eye pieces that can be used because of the need to fit inside the headband when not in use. Since these eye pieces are too small and too flat to adequately follow the contours of the head and face, unfiltered sunlight as well as foreign objects are allowed to reach the eyes from the sides and bottoms of the eye pieces.

A later attempt to solve the problem of protecting the eyes from unfiltered sunlight and foreign objects was attempted by U.S. Pat. No. 4,852,189, issued to Duggan in August 1989, by using a one piece wrap around eye piece held in place by a hook and loop attachment to the headband. Although the eye piece gave better eye protection, it was still cumbersome and unwieldy to operate by requiring two hands to change the position of the eye piece.

A more logical attempt was provided in U.S. Pat. No. 5,105,475, issued to Lynd on Apr. 21, 1992, by providing a wrap around eye piece that rotates up and down by means of two arms attached to the headband. However, each arm of the eye piece was unfortunately attached to the headband with a single rotation point. This single rotation point eliminated the ability of the eye piece to tilt as it was rotated, thereby not allowing the eye piece to more closely follow the contour of the head and face of the wearer. Also no tensioning device was provided to keep the eye piece held firmly in place in the two desired positions. And finally, the eye piece had to rotate into a cap bill, thus limiting its travel, making the design unsuitable for a vigorous sport like basketball.

The present invention uses a new approach to the old problem of combining a contoured optical eyeshield and a headgear, such as a sweatband. The present invention allows the wearer to enjoy the benefits of a sweatband plus the benefits of a lightweight, comfortable eyeshield that stays in place during rigorous activities, and then stays fashionably above the forehead when not needed by means of a unique bistable tensioning pivotal mechanism. The forces needed to keep the eyeshield in place are more efficiently applied downward on the increasing slope of the nose rather than like normal glasses exerting forces upward on the decreasing slope of the nose and inward toward the back of the head. The bistable tensioning pivotal mechanism allows the nose piece to become a self adjusting support that fits the eyeshield to a wide variety of faces. Not only is less force needed with this approach, but the bistable tensioning pivotal mechanism distributes the forces comfortably throughout the circumference of the sweatband and comfort is greatly enhanced. The eyeshield may also be adjusted in relation to the face of the user.

Until now, the hand motion needed to slip up other eye glasses designs required an awkward twisting motion of the hands and wrists. The natural movement of the hands to rotate this invention's eyeshield is accomplished with a simple upward motion of one hand or the fingers.

With the recent upsurge of interest in outdoor sports, especially outdoor basketball, a real need is developing for an athletic sweatband/sunglasses apparel combination that realistically provides the comfort, protection, and style demanded by the modern athletes. Until now, no rotating sunglasses/sweatband combination has proved widely acceptable to the athletic glasses market.

SUMMARY OF INVENTION

The above referred to previous patents have illustrated the need for a one piece sweatband/sunglasses apparel combination that is comfortable and adjustable, sturdy, functional and attractive to wear.

Accordingly it is a feature of the present invention to provide a protectable eyeshield pivotally connected to a headgear by a pair of pivotal arms each having a bistable tensioning pivotal mechanism incorporating a single stretchable elastic band formed as a loop and disposed in tension about and between the pivotal arms to apply maximum retention force to the arms at their position of use and non-use of the eyeshield.

According to a further feature of the present invention is the step of selectively supplying different strength elastic bands affording the user's option to vary maximum tensile forces during operation of the eye shield between positions of use and non-use.

According to a still further feature the eyeshield is adjustable with respect to the face of a wearer to fit various face configurations and to provide more comfort to the user.

According to a further feature the headgear is a terry cloth type sweatband that absorbs perspiration, keeps the hair in place, provides comfortable support for the eyeshield's bistable tensioning pivotal mechanism and wherein the sweatband has an elastic strap with adjusting buckles that provides a one size fits all capability.

Another feature is to provide a one piece contoured tinted optical quality eyeshield that is curved to closely emulate the shape of the face, thereby protecting the eyes from unfiltered sunlight as well as the introduction of foreign objects.

A further feature is to provide a bistable tensioning pivotal mechanism that applies force to keep the eyeshield down in place in the normal viewing position; then decreases the force to zero as the eyeshield is manually lifted upward toward the forehead, and then applies increasing force in the opposite direction to keep the eyeshield securely up in the out of viewing position above the forehead.

Another feature is to provide a smooth, fluid feel associated with the raising and lowering of the eyeshield due to the bistable tensioning pivotal mechanism.

Still another feature is to provide a capability of easily removing the optical eyeshield's bistable tensioning pivotal mechanism from the sweatband so the sweatband can be machine washable.

A further feature is to provide a pivotal eyeshield secured to an adjusting mechanism to vary the position of the eyeshield in front of the wearer's face.

According to the above features, from a broad aspect, the present invention provides an eye protection device comprising an eyeshield pivotally connectable to a headgear by a pair of bistable tensioning pivotal mechanisms to position said eyeshield to an eye protection position of use and to a position of non-use away from the eyes of a wearer, each said mechanisms having a pair of pivotal arms pivotally connected at one end to a support base which is attachable to said headgear, each arm of said pair of pivotal arms having a free end pivotally connected to said eyeshield, said pivotal arms having a band engaging guide means secured to each said arm at a predetermined location with respect to a respective one of said first and second pivot connections and displaceable on an arc about said respective one of said first and second pivot connections, a single stretchable elastic band formed as a loop and disposed in tension about and between said band engaging guide means of said pair of pivotal arms to exert a pulling force in opposed directions to displace said arms in tandem between said position of use and non-use, and abutment means associated with said pair of pivotal arms to arrest said arms at said position of use and position of non-use.

Another feature of the invention, in accordance with that set forth above, is the novel method of selectively providing one of a plurality stretchable elastic bands whereby the user has the option of incorporating different tensile force in the operating mechanism of the bistable tensioning mechanism between positions of use and non-use.

According to a still further broad aspect of the present invention there is also provided an eye protection device, comprising in combination:

(a) a headband adapted to engage the head of a user to support said eye protection device;
 (b) an optical eyeshield having a right side portion and a left side portion;
 (c) a first and second bistable eyeshield support rigidly connected to the right and left side portion respectively of said headband, each said bistable eyeshield support including:
  i. a base rigidly connected to a side portion of the headband,
  ii. an upper arm having an outer end pivotally connected to an upper point of said side portion of the eyeshield and an inner end pivotally connected to a first pivot point of said base,
  iii. a lower arm having an outer end pivotally connected to a lower point of said side portion of the eyeshield and an inner end pivotally connected to a second pivot point of said base, said second pivot point of said base being below said first pivot point of said base,
  iv. a low friction guide connected to a support point of said base rearward of said first and second pivot points thereof, below said first pivot point of said base, and above said second pivot point of said base,
  v. an elastic band having an upper segment engaging said low friction guide and an intermediate point of said upper arm, and a lower segment engaging said low friction guide and an intermediate point of said lower arm,
 the upper segment of said elastic band producing a first tensile force between said low friction guide and the intermediate point of said upper arm, the lower segment of said elastic band producing a second tensile force between said low friction guide and the intermediate point of said lower arm,
 portions of said elastic band stretching around said low friction guide to the lower segment of said elastic band as the eyeshield is raised from a lower position of use to an upper position of non-use
 portions of said elastic band stretching around said low friction guide to the upper segment of said elastic band as the eyeshield is lowered from an upper position to said lower position,
 the first and second tensile forces being balanced by the movement of the portions of said elastic band around said low friction guide as the eyeshield moves from one of the lower and upper positions through a bistable point to the other of the lower and upper positions.

According to a further aspect of the invention is the method provided whereby the user is afforded the option of selecting one of different strength elastic bands depending upon conditions of prospective use of the eye protective devices.

According to a still further broad aspect of the present invention there is provided an eye protection device comprising an eyeshield pivotally connectable to a headgear by a pair of bistable tensioning pivotal mechanisms to position said eyeshield to an eye protection position of use and to a position of non-use away from the eyes of a wearer, each said mechanisms having a pair of pivotal arms pivotally connected at one end to a support base which is attachable to said headgear, each arm of said pair of pivotal arms having a free end pivotally connected to said eyeshield, spring biasing means secured to each said arm at a predetermined location with respect to a respective one of said first and second pivot connections, said spring biasing means exerting a pulling force in opposed directions to displace said arms in tandem between said position of use and non-use, abutment means associated with said pair of pivotal arms to arrest said arms at said position of use and position of non-use, said support base being adjustably secured to said headgear by a position adjusting mechanism whereby to cause relative displacement of said eyeshield with a frontal position of said headgear.

According to a still further broad aspect of the present invention there is provided a eye protection device which comprises an eyeshield pivotally connectable to a headgear by a pair of bistable tensioning pivotal mechanisms to position the eyeshield to an eye protection position of use and to a position of non-use away from the eyes of a wearer. Each of the mechanisms has a pivotal arm pivotally connected at one end to a support base which is attachable to the headgear. The arm has a free end connected to the eyeshield. The pivotal arm has a first band engaging guide means secured at a predetermined location with respect to a pivot connection which secures the arm to the support base. The arm is displaceable on a arc about the pivot connection. A second band engaging guide means is secured to the support base at a predetermined location with respect to the pivot connection. A stretchable elastic band, formed as a loop, is disposed in tension about and between both of the band engaging guide means to exert a pulling force in opposed directions to displace the arms in tandem between the position of use and non-use. Abutment means is provided to arrest the arm at the position of use and the position of non-use.

Still further features and advantages will become more apparent from a consideration of the ensuing description and drawings.

BRIEF DESCRIPTION OF DRAWINGS

FIG. 5 is the cross-section view showing details of a screw mounting design that attaches the bistable tensioning pivotal mechanism to the sweatband;

FIG. 6 is an exploded view illustrating how the bistable tensioning pivotal mechanism is secured to the sweatband/adjustable elastic strap combination, typical for both sides of the sweatband;

FIG. 7-B is an exploded view of the bistable rotating mechanical tensioning system for the right side of the sweatband showing the back side of the pivotal arms;

DESCRIPTION OF PREFERRED EMBODIMENTS

Figure 1:
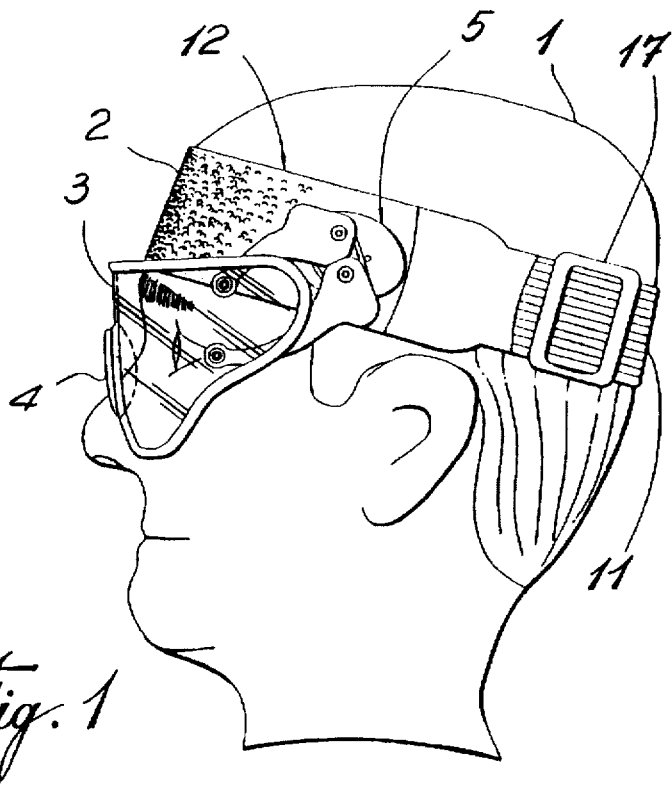
FIG. 1 is a side view of the present invention installed on the head of the wearer with the eyeshield down in the normal viewing position.

The present invention is comprised of three basic parts: a) a headgear in the form of an annular sweatband/adjustable elastic strap combination 12 which has a plastic headband insert 9 sewed inside the sweatband 2 to conform to the shape of the wearer's forehead, b) the eyeshield 3 which is a one piece optical quality polycarbonate, contoured shield to follow the shape of the wearer's head and face, and c) the bistable tensioning pivotal mechanism, one for each side of the sweatband, which rotates the eyeshield 3 and supplies tension to hold the eyeshield 3 in the normal viewing position of use and the out of viewing position of non-use. In a further broad aspect the eyeshield is adjustable relative to a frontal portion of the headgear to move it towards and away from the wearer's face.

FIGS. 1 to 5 show a headgear in the form of a sweatband/adjustable elastic strap combination 12 secured on the head of the wearer 1 and consists of four basic parts: the sweatband 2, the elastic strap 11 with adjusting buckle 17, the eyeshield 3 and the bistable tensioning pivotal mechanism 5.

The sweatband 2 is made of a material that is highly absorbent to keep perspiration out of the eyes of the wearer. The material should be light weight, able to dry quickly after use or washing, and feel soft and comfortable on the head. The sweatband 2 is 1¾" wide to supply maximum frictional area support between the head of the wearer and the bistable pivotal mechanism 5, and is made of terry cloth type material for comfort. FIG. 6 shows the plastic headband insert 9 sewed inside the sweatband 2 and the two open ends of the sweatband 2 sewed to the two ends of the elastic strap 11, through the plastic headband insert 9. The heat shrink tubing is used to cover the area, where the sweatband 2 and the elastic strap 11 are joined, and to give the area a finished appearance.

The plastic headband insert 9 houses the two eyelets 13 used to mount the bistable tensioning pivotal mechanism 5 to the sweatband 2 by means of the two mounting screws 8. The two eyelets 13 are installed into the plastic headband insert 9, through the sweatband outside layer 2A, FIG. 5, and the sweatband inside layer 2B, FIG. 5, providing a pathway for the mounting screws 8 to reach the threaded mounting holes in the base 21, FIG. 7-A and FIG. 7-B, of the bistable rotating tensioning pivotal mechanism 5.

FIG. 6 shows the 1¾" wide, 16" long, 0.060" thick plastic headband insert 9 inserted into the sweatband 2 and sewed inside 10 the sweatband 2 to give the sweatband 2 the shape to conform to the wearer's forehead 1, and to serve as the support for mounting the bistable tensioning pivotal mechanism 5. The plastic headband insert 9 is sewed inside 10 the sweatband 2 for approximately ¾ of the circumference from slightly behind one ear, around the forehead to slightly behind the opposite ear. The path of the sewed thread 10 follows the outline of the plastic headband insert 9 approximately ⅛" inside its edge, securing together the plastic headband insert 9, the sweatband 2, and the elastic strap 11 with adjusting buckles 17.

Figure 3:
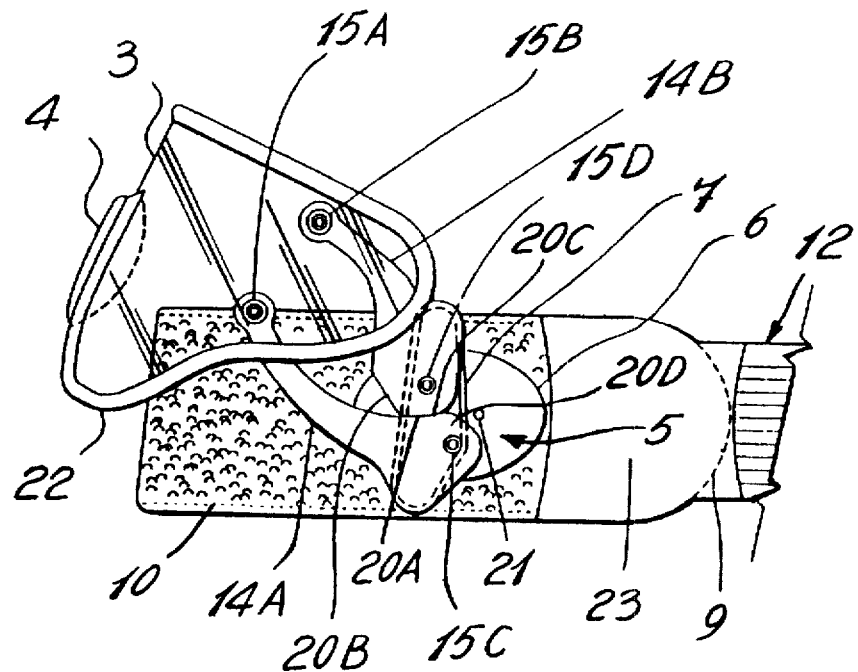
FIG. 3 is a side view showing the details of operation of the rubber band activated bistable tensioning pivotal mechanism attached to a sweatband type headgear and with the eyeshield up in the out of viewing position.
Figure 4:
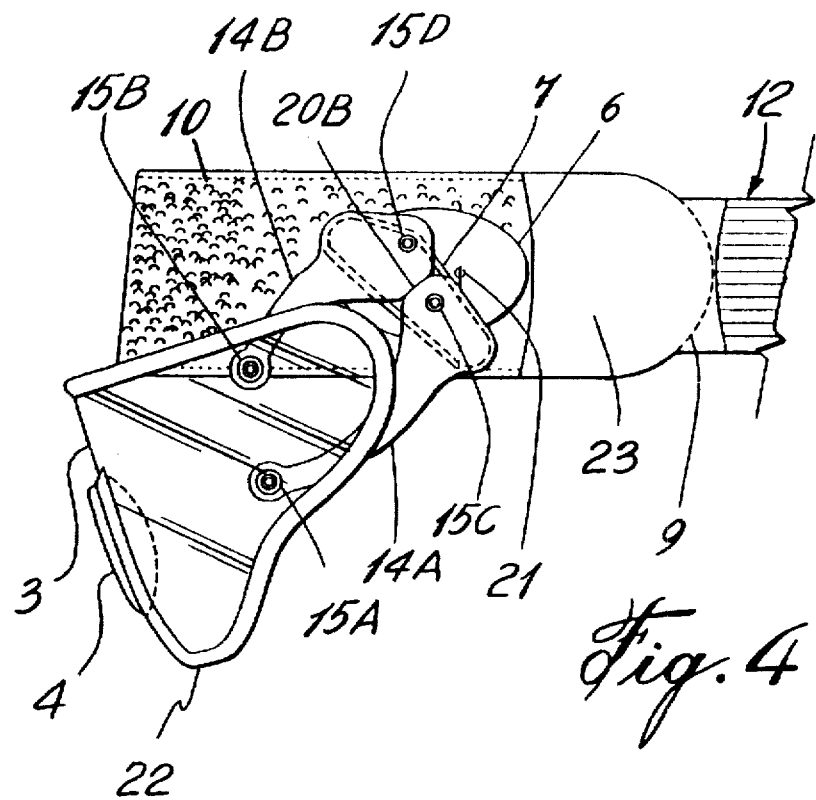
FIG. 4 is a side view showing the details of operation of the rubber band activated bistable tensioning pivotal mechanism attached to the sweatband and with the eyeshield down in the normal viewing position.
Figure 15:
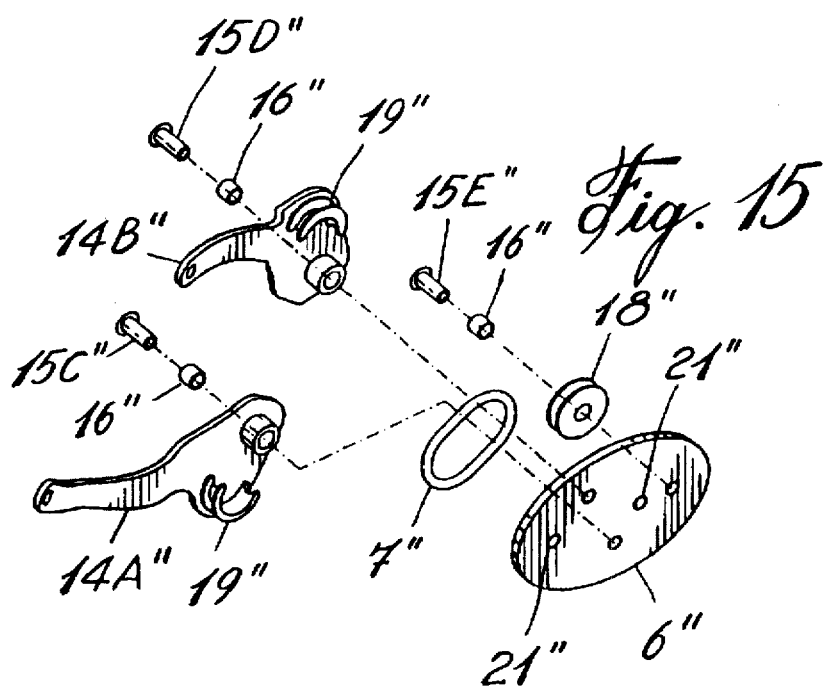
FIG. 15 is an exploded view illustrating the construction of the still further embodiment of the bistable tensioning pivotal mechanism.

The eyeshield 3, FIGS. 3 and 4, is a one piece curved polycarbonate type plastic shield of optical quality, and shaped to conform to the forehead, nose, and cheekbone areas of the face, approximately 9½" in length, heat formed into an approximate 4" radius, and 3" wide at the widest section. The edges are smooth and rounded, and without supporting frames, allowing a soft protective rubber trim 22 to be applied to the edges if deemed necessary for player safety. The eyeshield 3 can be clear as well as tinted to protect the eyes from the harmful effects of ultraviolet and infrared radiation from the sun encountered during outdoor sports. The thickness of the plastic will depend upon its ultimate use, but a 0.060" thickness has proven to be a good balance between strength and weight. A soft nosepiece 4 made of lightweight foam rubber provides support for the eyeshield as well as a locating device to properly locate the eyeshield 3 relative to the face of the wearer. The eyeshield 3 is attached to the bistable tensioning pivotal mechanism 5 by means of the two pairs of ⅛" diameter rivets 15A and 15B. These rivets 15A and 15B are inserted through ⅛" I.D. spacers 16", as shown in FIG. 15, and located between the eyeshield 3 and the swing arms 14A and 14B to assure smooth rotation with a minimum of friction between the eyeshield 3 and the swing arms 14A and 14B.

The two pairs of swing arms 14A and 14B are made of 0.031" thick 2024 aircraft grade aluminum with one ⅛" diameter hole drilled in each end for mounting to the eyeshield 3 by means of the rivets 15A and 15B, and one ⅛" diameter hole drilled in each opposite end for mounting to the bistable tensioning pivotal mechanism 5 by means of rivets 15C and 15D. Black anodizing may be used to produce a non-glare surface for these aluminum parts. The arms may also be molded from suitable plastics material.

Each of the two bistable tensioning pivotal mechanism 5, one on each opposite side of the sweatband 2, is built upon a 1⅛" wide×2" long×3/32" thick oval shaped aluminum or plastic base 6 which is secured to the plastic headband insert 9 inside the sweatband 2 by means of the two mounting screws 8.

Figure 7B:
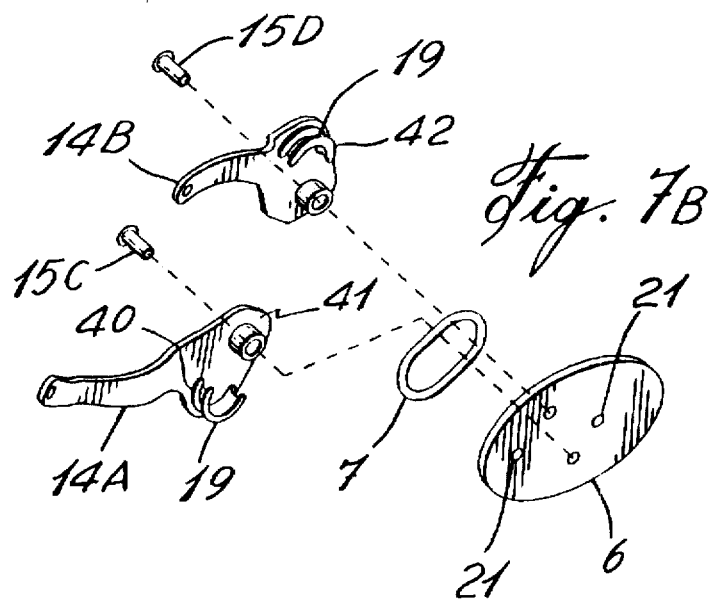
FIG. 7-A is an exploded view of the bistable rotating tensioning pivotal mechanism for the left side of the sweatband.

Referring now to FIGS. 3, 4, 7-A, 7-B and 8 and 9, there will be described the construction operation of the bistable tensioning pivotal mechanism 5. As shown more clearly in FIG. 7-B, each of the pivotal arms 14A and 14B are provided with a band engaging guide means 19 formed as an arcuate convexly curved guide surface 40 extending from the back wall 41 of the pivotal arms and having opposed transverse flange walls 42 whereby to form an arcuate guide channel for retaining a portion of the elastic band 7 positioned in tension thereabout. The inner flange 42 may be formed by the inner surface 41 of the swing arms if the part is injection molded. A small sheave could also be substituted to achieve the same purpose.

Figure 8:
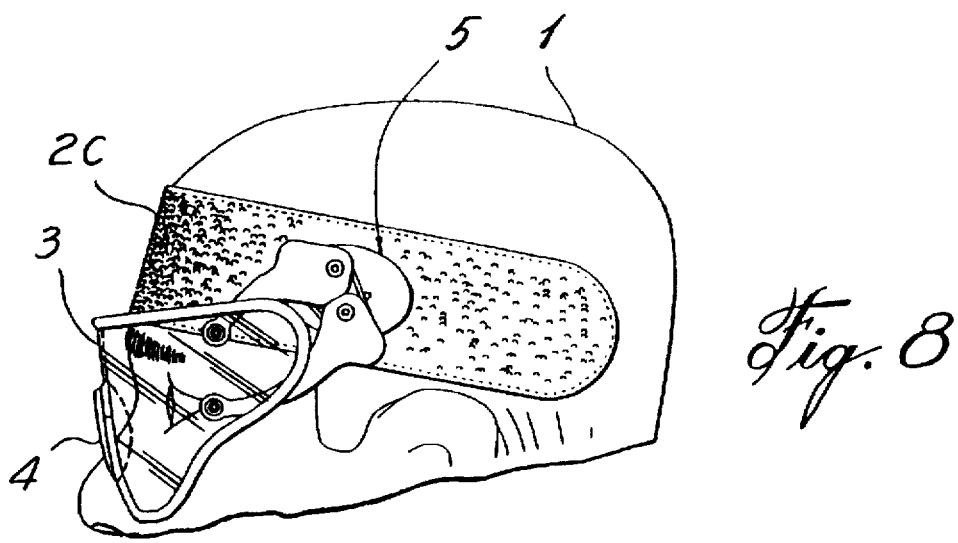
FIG. 8 is a side view of a U-shape sweatband installed on the head of a wearer with the eyeshield down in the normal viewing position.
Figure 9:
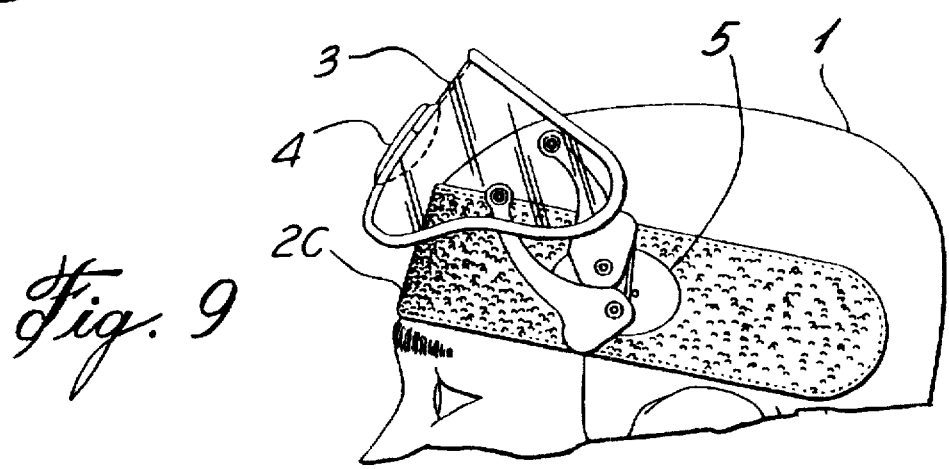
FIG. 9 is a side view of the U-shape sweatband installed on the head of a wearer with the eyeshield up in the out of viewing position.

As hereinshown the swing arms 14A and 14B are each pivotally secured to pivot connections 15D and 15C which are pivotally secured to the support base 6. The free end of the arms is also pivotally connected to the eyeshield by a pair of rivets 15A and 15B or simply by a pair of slotted pivot pins which permit easy removal of the swing arms from the shield, as is necessary to remove the elastic band from the bistable tensioning pivotal mechanism 5. The elastic band 7 is formed as a loop and is dimensioned so that when positioned about the guide surfaces 40 of the guide element 19 it stretches to apply a tension between the guide elements of the pair of pivotal arms 14A and 14B to exert a pulling force in opposed direction when the arms are displaced on their pivot connections 15C and 15D whereby the arms are displaceable in tandem between a position of use as shown in FIG. 8 with the eyeshield protecting the eye area of the wearer and to a position of non-use, as shown in FIG. 9, with the eyeshield pivoted above the eye area in front of the forehead of the wearer. These positions of use and non-use are determined by abutment means incorporated into the shape of the pivotal arms and is comprised by a first and second shaped abutment lower edge formation 20A and 20B respectively for the upper one of the pair of side arms and a first and second shaped abutment upper edge formations 20C and 20D,. respectively, of a lower one of the pair of pivotal arms 14A and 14B. The first abutment formation 20A of the upper arm and lower arms are in abutment relationship and arrest the arms at the position of non-use, as shown in FIGS. 3 and 9 while the second abutment formations 20B and 20D are in abutting relationship and arrest the arms at the position of use. The shape of these formations therefore determine these positions.

As shown in FIG. 3, the pivot connections 15C and 15D are spaced apart and offset from one another in the vertical plane. In this particular embodiment the elastic band 7 is positioned about the post of these pivot connections. The band 7 has a predetermined tensile strength depending on the force that one wishes to exert on the arms and their maximum position of use position of non-use. By interchanging these bands with other bands of different tensile strengths, this pulling force on the arms can be modified by the user. This affording a novel method whereby the operating forces between positions of use and non-use of the device can be optionally altered depending upon conditions of prospective use. The band is detachable from the arms by detaching the free end of the arms from the eyeshield and passing the band over the pair of arms. Accordingly, it is very simple to replace a band to use one with more strength, if desired, depending on the type of support that the eyeshield is used for or to replace a defective band.

It is pointed out that with the bistable tensioning pivotal mechanism as hereinshown the maximum pulling force on the arms and consequently the eyeshield is the position of use and position of non-use of the eyeshield and this force progressively diminishes as the eyeshield is displaced with the fingers of the wearer towards a substantially mid-way position where the pulling force is at a minimum or null point. It is pointed out that although the headgear as hereinshown is a sweatband or headband 2, it can be other types of headgear onto which the bistable tensioning pivotal mechanism 5 can be secured and it is therefore intended not to restrict this invention to a sweatband type headgear.

A unique feature of the bistable tensioning pivotal mechanism 5, aside from its simplicity which is one of its main characterizing features, is the fact that when it is displaced with the hands it has a smooth-continuously variable "feel" as the eyeshield is rotated between its position of use and position of non-use or vice-versa. This smooth "feel" is accomplished by the change of the relative positions of the two guide elements 19, not only to each other, but also with relation to the two pivot connections 15C and 15D of the swing arms.

When the eyeshield 3 is in the position of use, its down position in front of the wearer's eyes, the two curve guide elements 19 are arranged in relation to the two pivot points wherein there is a maximum moment on the upper swing arm and a nearly zero moment on the lower swing arm due to its alignment with the pivot connection 15C. When the eyeshield is up in its position of non-use, the two curve guide elements are arranged in relation to the two pivot points whereby the upper curve guide element is at zero or nearly zero moment on the upper swing arm due to its alignment with the pivot connection 15D and the curve guide element of the lower swing arm is at its maximum moment. These maximum forces hold the shield in both these positions and as the resultant force is decreased to zero substantially mid-way in the travel when displacing the eyeshield, this pulling force begins to increase progressively in the opposite direction as the eyeshield moves to the opposite position. Therefore, since the forces are infinitely variable, the "feel" of the bistable tensioning pivotal mechanism is a continuously smooth application of increasing or decreasing force in the two opposite directions.

Figure 10:
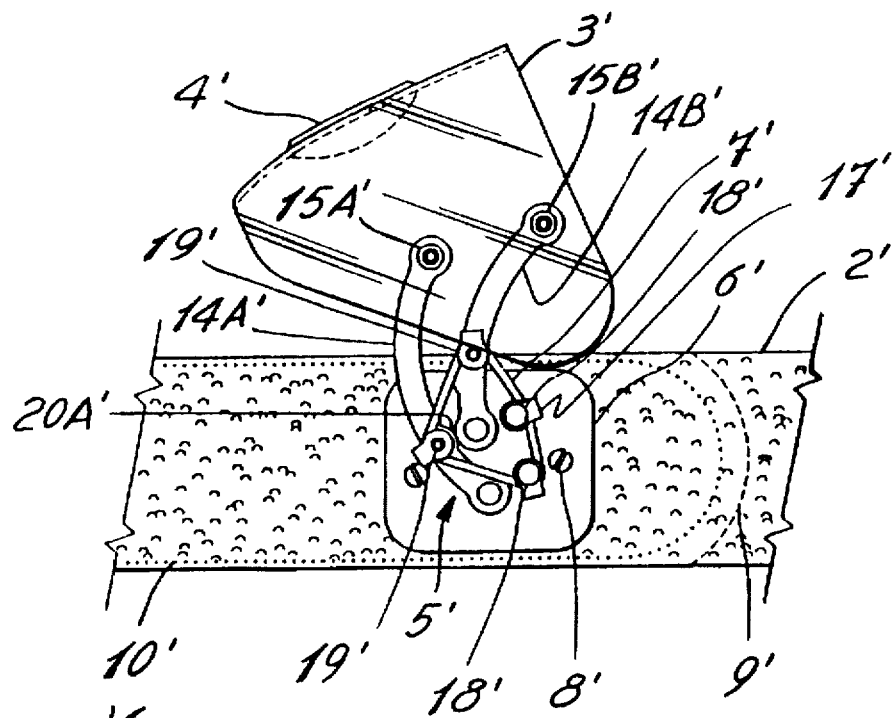
FIG. 10 is a side view similar to FIG. 3 but illustrating a further embodiment of the bistable tensioning pivotal mechanism.
Figure 11:
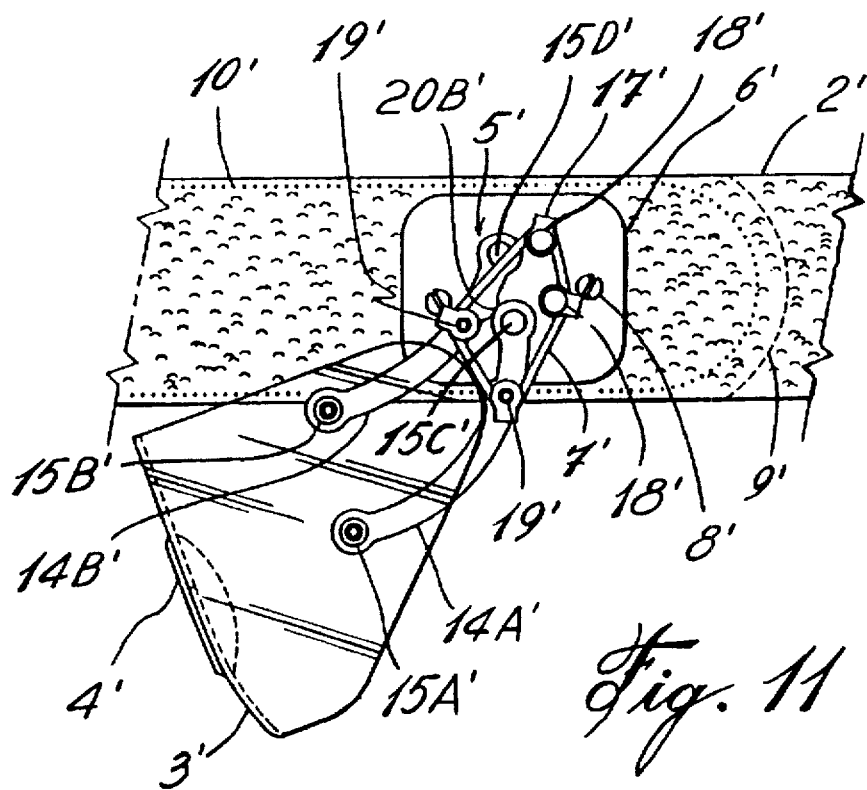
FIG. 11 is a side view similar to FIG. 4 of the further embodiment of the bistable tensioning pivotal mechanism.
Figure 12:
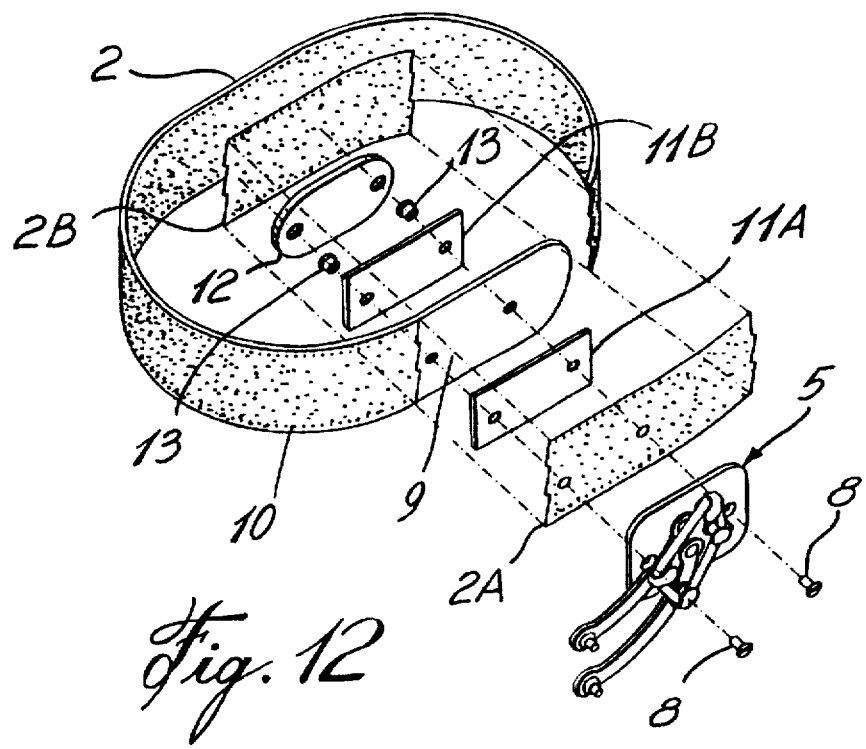
FIG. 12 is an exploded view similar to FIG. 6 of the further embodiment of the bistable tensioning pivotal mechanism.

With reference now to FIGS. 10 to 12, there will be described a further embodiment of the bistable tensioning pivotal mechanism 5' as hereinshown. Like reference numerals as in FIGS. 1–9 have been given a prime designation and the description of some of these will not be repeated. The tensioning pivotal mechanism 5' consists of two stationary posts 18' attached to the plastic base 6' and two rotating posts 19' attached to the two swing arms. The lower swing arm 14A' is attached to the plastic base 6' by means of the rivet 15C'. The upper swing arm 14B' is attached to the plastic base 6' by means of the rivet 15D'. The rubber band 7' is stretched around the two stationary posts 18' and the two rotating posts 19', FIG. 10 and FIG. 11, and held in place by a keeper 17' installed in the top of each of the two stationary posts 18' and the two rotating posts 19'. The keepers 17' have mounting holes which allow to pass therethrough and the flared end of the rivets holds the keepers 17' in place atop the stationary posts 18' and the rotating posts 19'. The rubber band 7' is approximately 0.080" thick, 3" in circumference in the static state, and rides on the surfaces of bushings on the stationary posts 18' and the rotating posts 19' to reduce friction.

The unique part of the invention is the bistable rotating mechanism tensioning system 5' which is used to mount the eyeshield 3' to the sweatband 2', and to give the apparatus a solid, fluid, feel as the eyeshield 3' is manually rotated up and down between the normal viewing position (FIG. 11) and the out of viewing position (FIG. 10). The position of the stationary posts 18' and the changing relative position of the rotating posts 19' on the swing arms 14A' and 14B' as the arms rotate around the mounting rivets 15C' and 15D' causes the rubber band 7' to apply tension to the eyeshield 3' in the normal viewing position (FIG. 11) to hold the eyeshield 3' firmly in place even during strenuous physical activity. When the eyeshield 3' is manually lifted toward the out of viewing position (FIG. 10), the position of the rotating posts 19' changes in relation to the stationary posts 18' and the tension applied to the eyeshield 3' decreased to zero midway through the travel path, then begins increasing again in the opposite direction until the eyeshield 3' is rotated to the out of viewing position (FIG. 10) where maximum tension is applied to keep the eyeshield 3' held firmly in this out of viewing position. The resultant force vectors from this arrangement force the swing arms 14A' and 14B' to rotate in a counter-clockwise direction around the mounting rivets 15C' and 15D' in the normal viewing position, rotate clockwise in the out of viewing position, as viewed in the figures and remain neutral midway in the travel arc.

The use of bushings in the swing arms 14A' and 14B', the two stationary posts 18' and the two rotating posts 19' provide a low friction path for the rubber band 7' to apply its forces smoothly and efficiently during its operation, giving the invention a solid, almost liquid fee as the eyeshield 3 is rotated.

The rubber band 7' which activates the mechanical tensioning pivotal mechanism is approximately 0.080" thick and has a circumference of approximately 3" in the static state, and provides the most efficient, lightweight, simple and economical solution of providing the force needed to hold the eyeshield 3' firmly in its desired positions, as compared to springs, cams, latches and other bulky mechanical systems. Another advantage of this mechanism, and all of its embodiments described herein, is that the operating characteristics of the system can be drastically changed by making small changes in the material composition and/or changes in the dimensions of the rubber band 7' alone. The rubber band 7' is kept in position on the stationary posts 18' and the rotating posts 19' by means of keepers 17', which are round aluminum or plastic parts with one leg bent down 90 degrees to keep the rubber band 7' in place even during the high impacts encountered during competitive sports activities. New rubber bands 7' can be installed by maneuvering the bands under the small clearance allowed between the keepers 90 degree leg and the plastic base 6'.

Figure 2:
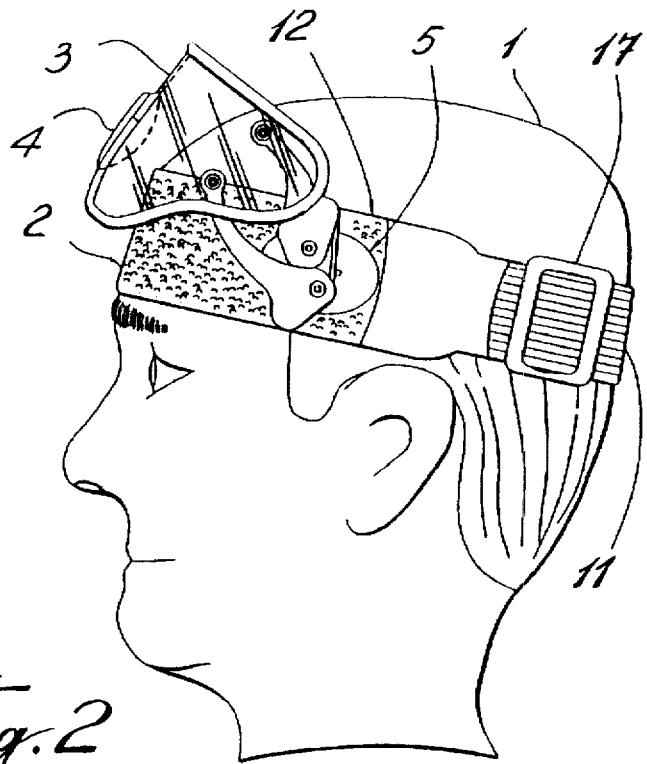
FIG. 2 is a side view of the present invention installed on the head of the wearer with the eyeshield up in the out of viewing position.

The offset locations of the pivot points for the upper swing arm 14B' and the lower swing arm 14A', for both the plastic base 6' and the eyeshield 3', where carefully determined so the eyeshield 3' would rotate with two degrees of freedom, allowing the eyeshield 3' to first rotate up and away from the face of the wearer, then begin tilting backward as it moves upward, until it rests comfortably above the wearer's forehead like a pair of normal sunglasses would be positioned (FIG. 2). Mechanical stops 20A', and 20B' incorporated into the swing arms 14A' and 14B' prevent the eyeshield 3' from over rotating in either the up or down positions.

The theory of operation of the bistable rotating mechanical tensioning system can best be described as the application of forces generated whenever a tension device, such as a rubber band, is deformed from its natural state. These forces then apply moments to the rotating posts on the two pairs of swing arms connecting the bistable rotating mechanical tensioning system to the eyeshield, causing the eyeshield to rotate between the normal viewing position and the out of viewing position.

The relative positions of the stationary posts and the rotating posts on the offset swing arms changes as the swing arms move through their respective travel arcs. when the eyeshield is in the normal viewing position (FIG. 11), the expanded rubber band applies tension to the rotating posts, which are now located below the pivot points of the swing arms, creating a counter clockwise moment on the swing arms, firmly holding the eyeshield in the normal viewing position. In this position, relative to the rotating posts, the stationary posts are also below the swing arms pivot points.

When the eyeshield is in the out of viewing position (FIG. 2), the expanded rubber band applies tension to the rotating post, which are now located above the pivot points of the swing arms, creating a clockwise moment on the swing arms, firmly holding the eyeshield in the out of viewing position. In this position, relative to the rotating posts, the stationary posts are also above the swing arms pivot points.

As the swing arms move to and from the positions just described, the moments applied to the swing arms by the rubber band decrease to zero as the rotating post, swing arms pivot points, and the stationary posts come into a straight line alignment. As these three points diverge relative to one another the moments applied to the swing arms begins to increase again in the opposite direction.

Figure 13:
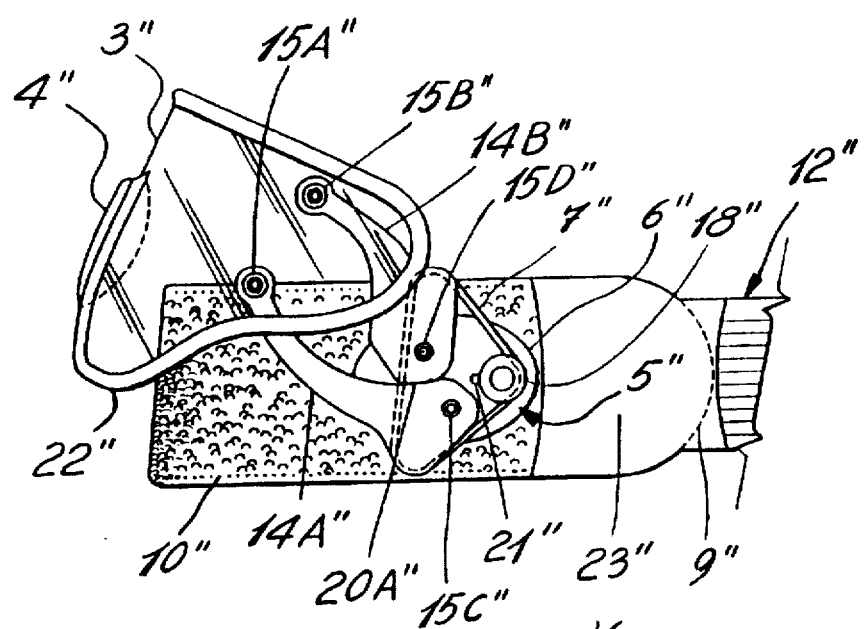
FIG. 13 is a side view similar to FIG. 10 of a still further embodiment of the bistable tensioning pivotal mechanism.
Figure 14:
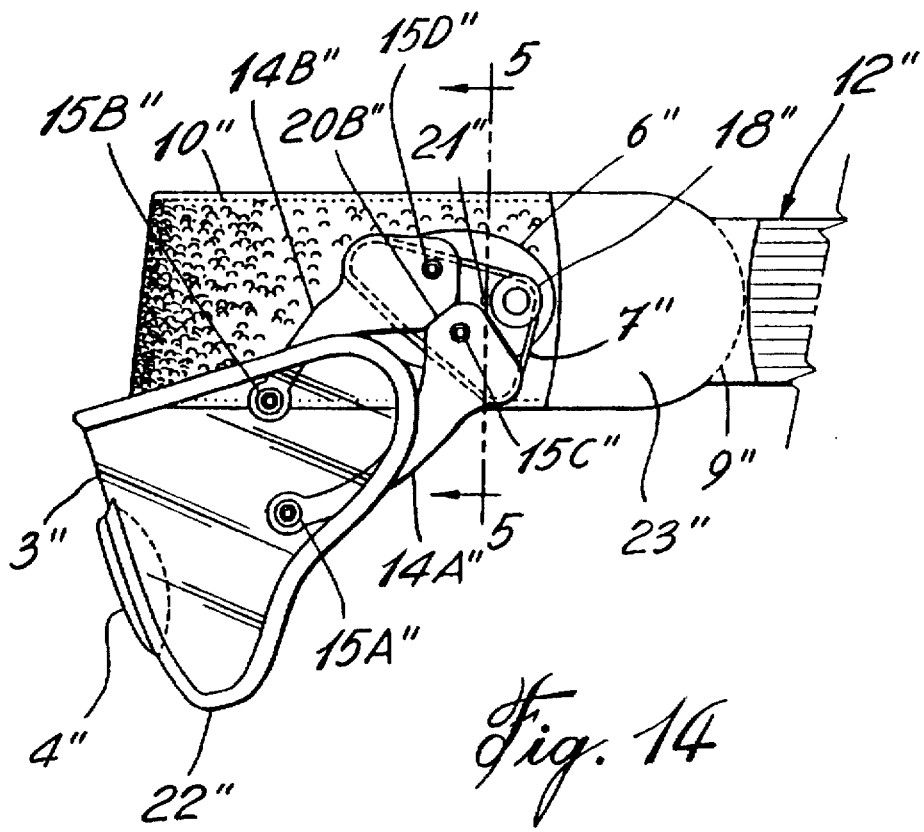
FIG. 14 is a side view similar to FIG. 11 of the still further embodiment of the bistable tensioning pivotal mechanism.

Referring now to FIGS. 13 to 15, there will be described a further embodiment of the bistable tensioning pivotal mechanism 5" of the present invention. Again, like numerals to those of FIGS. 1–9 will be given a double prime designation and the description of some of these will not be repeated. As hereinshown, the mechanism consists of one pulley 18" attached to the base 6" by means of rivet 15E", and two curved guides 19" on the two swing arms 14A" and 14B". The lower swing arm 14A" is attached to the base 6" by means of the rivet 15C" and a spacer 16". The upper swing arm 14B" is attached to the base 6" by means of the rivet 15D" and a spacer 16". The rubber band 7" is stretched around the pulley 18" and the two curved guides 19", see FIG. 15. The rubber band 7 is approximately .070" thick, 3" in circumference in the static state, and rides in the groove of the pulley 18" and the groove of the curved guide 19" of the lower swing arm 14A" and the groove of the curved guide 19" of the upper swing arm 14B".

The position of the one pulley 18", FIG. 13 and FIG. 14, and the changing relative position of the curved guides 19" on the swing arms 14A" and 14B" as the arms rotate around the mounting rivets 15C" and 15D" causes the rubber band 7" to apply tension to the eyeshield 3" as previously described. The pulley 18" provides a low friction path for the rubber band 7" to apply its forces smoothly and efficiently to the two curved guides 19" of the lower swing arm 14A" and the upper swing arm 14B" during its operation, giving the invention a smooth, fluid feel as the eyeshield 3" is rotated. The rubber band 7" is kept in position by means of the alignment of a single deep groove in the pulley 18", and a single deep groove channel in the curved guide 19" of the lower swing arm 14A", and a single deep groove channel in the curved guide 19" of the upper swing arm 14B". This alignment of the rubber band 7" will keep the rubber band 7" in place even during the high impacts encountered during competitive sports activities.

The offset locations of the pivot points for the upper swing arm 14B" and the lower swing arm 14A", for both the base 6" and the eyeshield 3", were carefully determined so the eyeshield 3" would rotate with two degrees of freedom, allowing the eyeshield 3" to first rotate up and away from the face of the wearer, then begin tilting backward as it moves upward, until it rests comfortably above the wearer's forehead like a pair of normal sunglasses would be positioned (FIG. 2). Mechanical stops 20A" and 20B" incorporated into the swing arms 14A" and 14B" prevent the eyeshield 3" from over rotating in either the up or down positions.

A second variation of the above described invention would involve having the sweatband conform solely to the size and shape of the interior plastic headband insert 9", thus eliminating the adjustable elastic strap 11" traversing the back of the head of the wearer (FIG. 8 and FIG. 9).

This variation of the above described invention involves only two physical changes: a) terminating the sewed sweatband at the two ends of the plastic headband insert 9", and b) increasing the material thickness of the plastic headband insert 9" from approximately 0.030" to approximately 0.060".

All other physical parts remain the same.

The installation and wearing features of this ¾ circumference sweatband solves the problem of the less active female and male wearer's who do not want their expensive hair styles disturbed by a full circumference sweatband/adjustable elastic strap combination 12".

This second variation of the above described invention has the advantage of being installed and worn beneath the overlaying hair of the wearer, without an adjustable elastic strap 11" matting and forming an indentation in the hair style at the back of the head of the wearer. The sweatband is inserted in place directly from the front of the head, rather than being pulled over the top of the head, thus eliminating the disarranging and matting of the wearer's hair.

The increased thickness of the plastic headband insert 9" creates a spring action, when installed in place, that gently grips the head of the wearer. With the additional support of the nose piece 4", and the tension supplied by the bistable tensioning pivotal mechanism 5", the invention is held securely in place during moderate physical activities, without matting or forming indentations in the hair stile of the wearer.

The bistable tensioning pivotal mechanism used to join the eyeshield to the sweatband is a rugged, light weight, and precise way to give the outdoor athlete the comfort, convenience and protection required by today's sports.

While the above description contains many specificities, these should not be construed as limitations on the scope of the invention, but rather as an exemplification of one preferred embodiment thereof. Many other variations are possible. For example, the bistable tensioning pivotal mechanism could be used for raising and lower welding hoods, safety glasses, ski goggles, reading glasses, virtual reality displays, tops to toy chests and jewelry boxes, etc. Also a soft expandable rubber boot or cover can be placed over the bistable rotating mechanical tensioning system to cover exposed edges and make the invention safe for high impact sports.

The sweatband can display art or advertising with all the possible color and graphic combinations. The aluminum swing arms can be replaced with plastic or composite materials for unusual applications. Changes in the parts sizes would allow the design to fit teen and pre-teen age groups.

Figure 16:
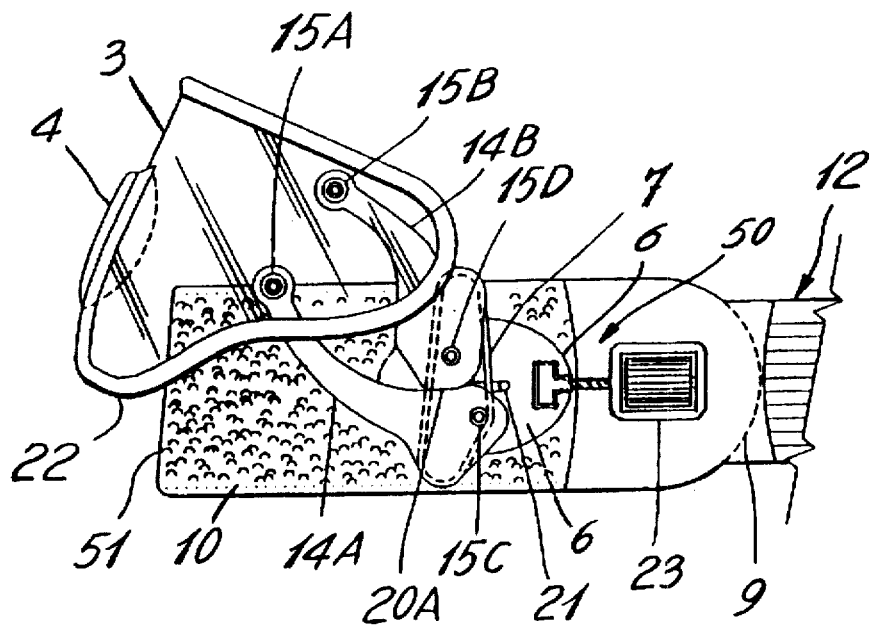
FIG. 16 is a side view illustrating the position adjusting mechanism to position the eyeshield to and away from a frontal portion of the headgear.
Figure 17:
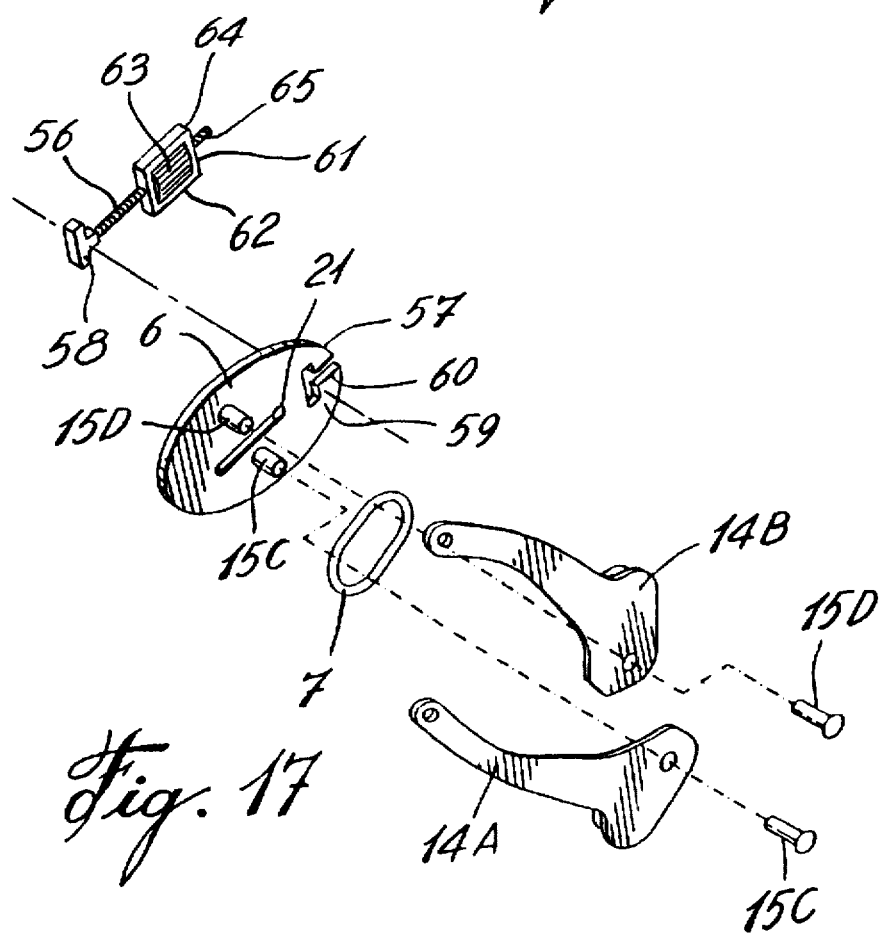
FIG. 17 is an exploded view showing the construction of the support base and the finger-actuable adjusting mechanism.
Figure 18:
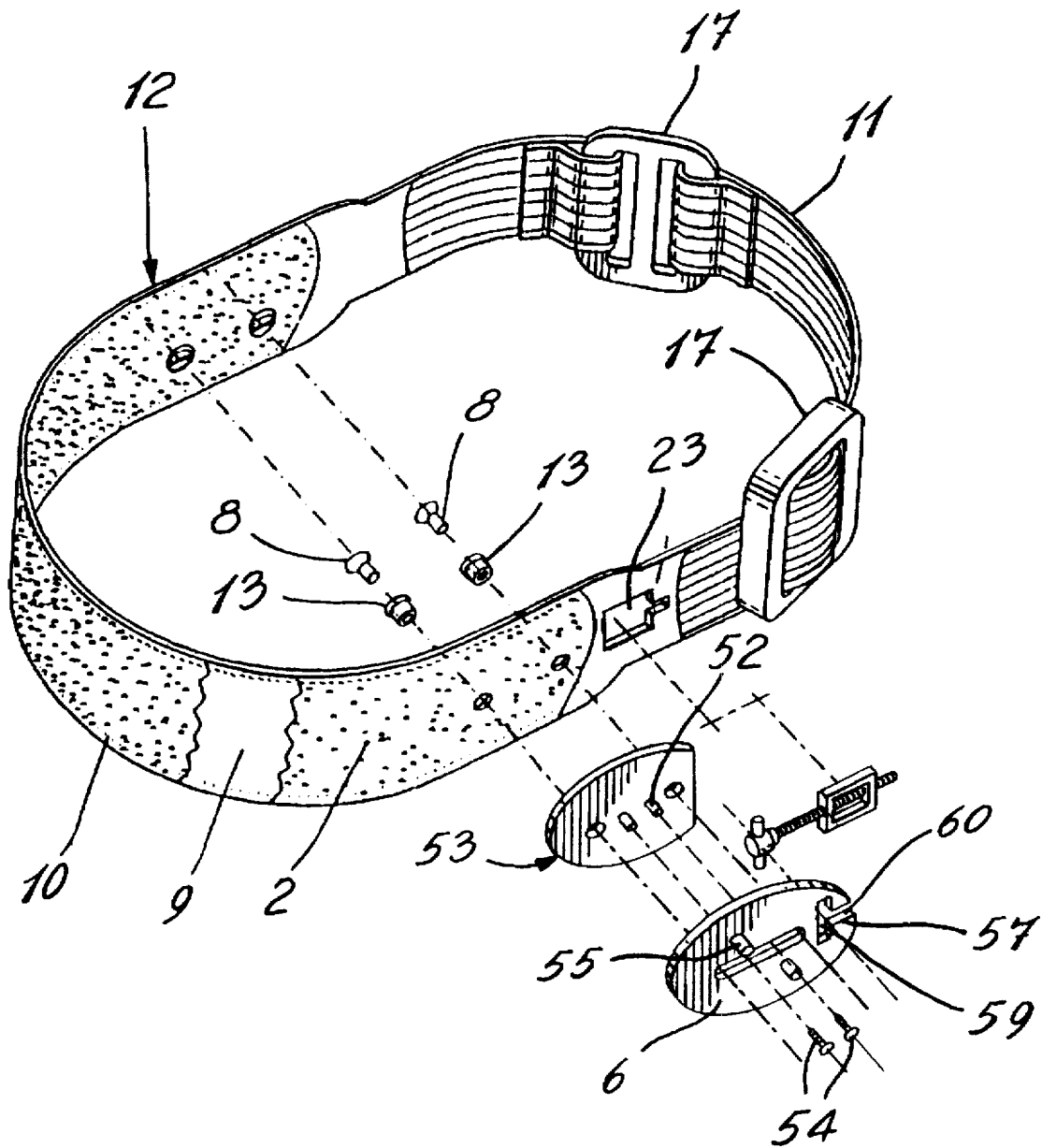
FIG. 18 is an exploded view showing a sweatband type headgear having the position adjusting mechanism secured thereto.

Referring now to FIGS. 16 to 18 there is shown a position adjusting mechanism 50 secured to the support base 6 to cause relative displacement of the eyeshield with respect to a frontal portion 51 of the headgear 12. The position adjusting mechanism 50 comprises essentially, as shown in FIG. 18, a mounting plate 53 which is secured to the headgear by the rivets and bushings 8 and 13. The mounting plate is provided with projecting abutment means in the form of guide posts 52 capable of receiving pop rivets 54 to secure the support base 6 in sliding movement thereover.

As hereinshown the mounting plate 6 is provided with an elongated slot 55 to permit limited longitudinal displacement of the support base over the mounting plate 53. The guide posts 52 determine the forward and rearward limit of this displacement and guide the plate along a straight axis.

An adjustment means in the form of a threaded shaft 56 is secured at a rear end 57 of the support base 6 in a variety of manner and as hereinshown this threaded shaft is provided with a flanged head 58 which is received in a transverse cavity 59 at the end of a through slot 60 thereby forming a T-shaped slot at the rear end 57 of the support base 6. Of course, this threaded shaft may also be integrally formed with the support base 6 and project rearwardly thereof.

The threaded shaft 56 extends through a stationary housing, herein formed as a U-shaped casing or housing 61 having an open end 62 and securable to a headgear. A finger actuable adjusting wheel 63 is disposed in this casing 61 and a shaft 56 is threaded therethrough by turning the wheel 63. This is done until the free end of the threaded shaft 56 extends through a hole (not shown) in the back wall 64 of the housing. Accordingly, the shaft 56 extends entirely through the housing with its free end 65 protruding therefrom at all times. The shaft 56 is of sufficient length to hold the wheel 63 captive between the side walls of the casing with the support base 6 in its maximum advance position. It can be seen therefore that by adjusting the position of the support base 6, the eyeshield 3 can be moved closer or further away from the wearer's face in front of his eyes. This is an adjustment which makes it possible to custom-fit the lens comfortably to the particular wearer and makes this eye protection device suit a great variety of people therefore making it universal. It can therefore also be appreciated that the combination of an eyeshield with pivotal arms secured to a base intentioned by biasing means and wherein the base is adjustable, is also a characteristic of the present invention clearly not taught by the prior art.

Figure 19:
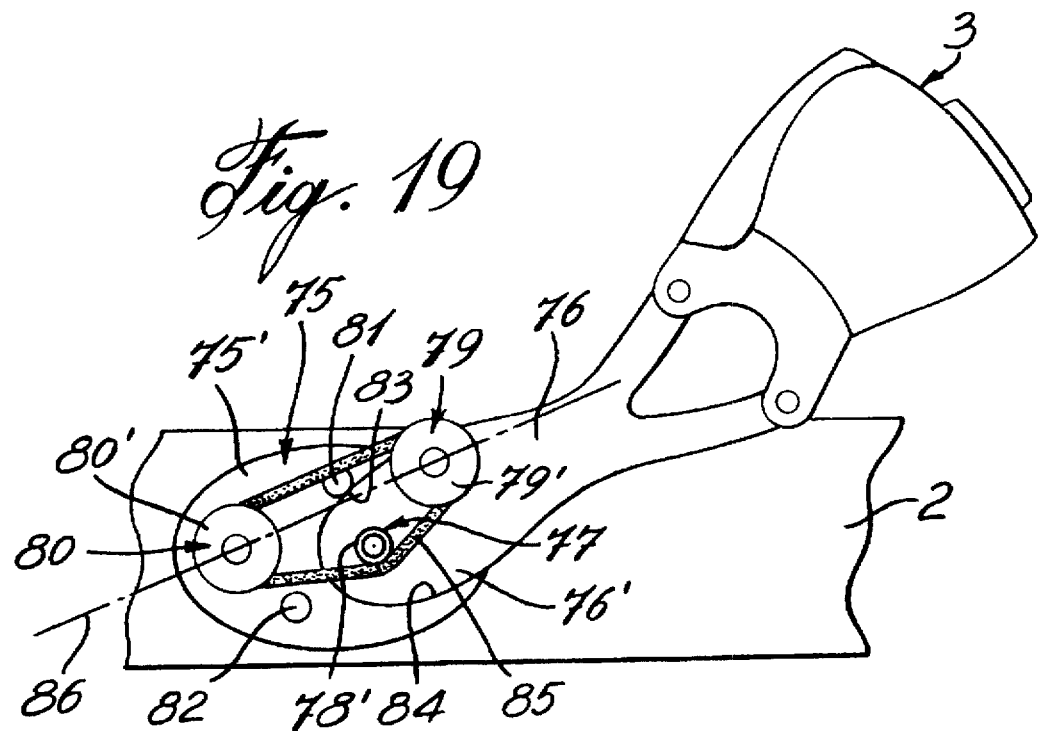
FIG. 19 is a fragmented side view illustrating a still further modification of the construction of the pivotal mechanism and the bistable tensioning pivotal mechanism.
Figure 20:
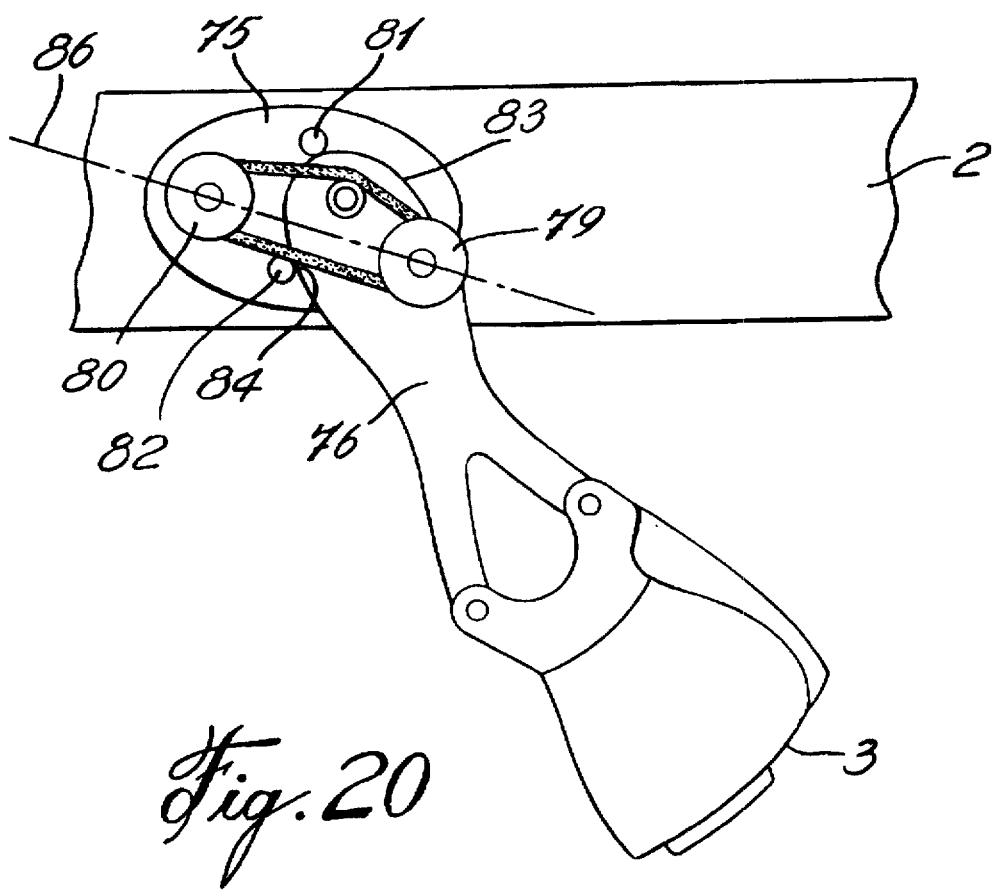
FIG. 20 is a view similar to FIG. 19 but with the eyeshield in position of use.

FIGS. 19 and 20 illustrate a still further variant of my invention. As hereinshown the eyeshield 3 is secured to the support base 75 by a single pivotal arm 76 which is pivotally connected to the base 75 by the pivot connection 77. The pivot connection 77 detachably secures the pivotal arm 76 to the base 75 and has a mounting screw 78 extending into a mounting post 77. The post 77 extends upwardly from the outer surface 76' of the pivotal arm 76. This single pivotal arm 76 replaces the two pivotal arms 14A and 14B as shown in FIG. 3 and performs the same function.

As hereinshown the pivotal arm has a first band engaging guide means in the form of a guide sheave 79 secured to the arm 76 at a predetermined position relative to the pivot connection 77. A second guide sheave 80 is also secured to the base 75 and also at a predetermined position with respect to the pivotal connection 77. First and second abutment means in the form of abutment posts 81 and 82, respectively, are also secured to the base 75 and extend above the outer surface 75' thereof a predetermined distance whereby to abuttingly engage with edge portions 83 and 84, respectively, of the pivotal arm 76 when the eyeshield 3 is in its position of non-use, as shown in FIG. 19 or its position of use, as shown in FIG. 20. The eyeshield 3 is brought to these positions by means of the stretchable elastic band 85 which is disposed between the guide sheaves 79 and 80 and engaged between the sheave walls, only the outer one 79' and 80' being shown in this drawing but obvious to a person skilled in the art. This elastic band is in tension about both of these sheaves and exerts a pulling force in opposed directions when the straight axis 86 passing through the center of the sheaves 79 and 80 is offset with respect to the pivotal connection 77.

As previously described, the elastic band 85 has a predetermined tensile strength to exert sufficient pressure to displace the eyeshield 3 to either position as shown in FIGS. 19 and 20 when the axis 86 is displaced with respect to the pivotal connection 77 either above or below same, as shown respectively at FIGS. 19 and 20.

The pivotal arm 76 has a predetermined contour shape to define the upper and lower edge formations 83 and 84, respectively, to arrest the eyeshield 3 at its desired position with respect to the sweat band 2. It is also pointed out that the eye protection device 3 as shown in FIGS. 19 and 20 is easily detachable from the base 75 by the removal of the single screw 78 at the pivot connection 77 as provided in both pivotal arms 76. Of course, the stretchable elastic band 85 is also removed from the guide sheaves. This permits for ease of maintenance repair or interchangeability of the eyeshield 3.

While my above description contains many specificities, these should not be construed as limitations on the scope of the invention, but rather as an exemplification of one preferred embodiment thereof. Many other variations are possible. For example, the bistable tensioning pivotal mechanism could be used for raising and lower welding hoods, safety glasses, reading glasses, virtual reality displays, tops to toy chests and jewelry boxes.

The sweatband can display art or advertising with all the possible color and graphic combinations. The aluminum swing arms can be replaced with plastic or composite materials for unusual applications. Changes in the parts sizes would allow the design to fit teen and pre-teen age groups.

Thus the scope of the invention should be determined by the appended claims and their legal equivalents, rather than by the examples given.

I claim.:

1. An eye protection device comprising an eyeshield pivotally connectable to a headgear by a pair of bistable tensioning pivotal mechanisms to position said eyeshield to an eye protection position of use and to a position of non-use away from the eyes of a wearer, each said mechanisms having a pair of pivotal arms pivotally connected at one end to a support base by a first and second pivot connection respectively, said support base being attachable to said headgear, each arm of said pair of pivotal arms having a free end pivotally connected to said eyeshield, said pivotal arms having a band engaging guide means secured to each said arm at a predetermined location with respect to a respective one of said first and second pivot connections and displaceable on an arc about said respective one of said first and second pivot connections, a single stretchable elastic band formed as a loop and disposed in tension about and between said band engaging guide means of said pair of pivotal arms to exert a pulling force in opposed directions to displace said arms in tandem between said position of use and non-use, and abutment means associated with said pair of pivotal arms to arrest said arms at said position of use and position of non-use.

2. An eye protection device as claimed in claim 1 wherein said elastic band is removably connected to about said band engaging means for replaceable connection thereto.

3. An eye protection device as claimed in claim 2 wherein said elastic band has a predetermined tensile strength, said band being interchangeable with other bands of different tensile strength to vary the strength of said pulling force.

4. An eye protection device as claimed in claim 2 wherein said free end pivotal connection of said arms is a detachable pivotal connection to permit the removal of said elastic band and the replacement of another elastic band.

5. An eye protection device as claimed in claim 1 wherein said pulling force is at a maximum at said position of use and said position of non-use and progressively diminishes as said eyeshield is displaced toward a substantially mid-way position where said pulling force is at a minimum.

6. An eye protection device as claimed in claim 1 wherein said abutment means comprises a first and a second shaped abutment lower edge formation of an upper one of said pair of arms, and a first and a second shaped abutment upper edge formation of a lower one of said pair of arms, said first abutment formation of said upper and lower arms being in abutting relationship and arresting said arms at said position of non-use while said second abutment formations of said upper and lower arms are in abutting relationship and arrest said arms at said position of use.

7. An eye protection device as claimed in claim 1 wherein said band engaging guide means is an arcuate convexly curved guide surface of a guide element secured to a back wall of each said pair of pivotal arms.

8. An eye protection device as claimed in claim 7 wherein said guide element is an arcuate guide wall having opposed transverse flange walls to form an arcuate guide channel for retaining a portion of said elastic band captive therethrough.

9. An eye protection device as claimed in claim 7 wherein said guide element is a cylindrical element.

10. An eye protection device as claimed in claim 1 wherein said headgear is a sweatband, said support base being secured to a rigid insert element.

11. An eye protection device as claimed in claim 10 wherein said support base is adjustably secured to said rigid insert element by a position adjusting mechanism whereby to cause relative displacement of said eyeshield with a frontal portion of said headband.

12. An eye protection device as claimed in claim 11 wherein said portion adjusting mechanism has a finger-actuable adjusting element to cause displacement of said support base along restraining guide means, and a threaded connector interconnecting said finger-actuable adjusting element and said support base.

13. An eye protection device as claimed in claim 1 wherein said support base is adjustably secured to said headgear by a position adjusting mechanism whereby to cause relative displacement of said eyeshield with a frontal position of said headgear.

14. An eye protection device as claimed in claim 1 wherein said free end of each said arms is pivotally connected to said eyeshield by a removable pivot pin to permit ease of disconnection of said free end from said eyeshield.

15. An eye protection device as claimed in claim 1 wherein said elastic band loop is also disposed about said first and second pivot connections.

16. An eye protection device as claimed in claim 1 wherein said bistable tensioning pivotal mechanism further comprises a pulley secured to said support base, said elastic band loop being positioned in tension about said pulley and said band engaging guide means of said pair of arms with said pivot connections disposed inside said loop in an off-set relationship.

17. An eye protection device as claimed in claim 13 wherein said position adjusting mechanism comprises a mounting plate secured to said headgear, said mounting plate having projecting abutment means extending through a slot in said support base to permit limited longitudinal displacement of said support base, and adjustment means to cause said displacement of said support base.

18. An eye protection device as claimed in claim 17 wherein said adjustment means comprises a threaded shaft secured at one end to said support base, said shaft extending through a stationary housing secured to said headgear and disposed in threaded engagement with a finger-actuable adjusting wheel arrested in said housing and partly accessible exteriorly of said housing.

19. An eye protection device, comprising in combination:

(a) a headband adapted to engage the head of a user to support said eye protection device;

(b) an optical eyeshield having a right side portion and a left side portion;

(c) a first and second bistable eyeshield support rigidly connected to the right and left side portion respectively of said headband, each said bistable eyeshield support including:

i. a base rigidly connected to a side portion of the headband, ii. an upper arm having an outer end pivotally connected to an upper point of said side portion of the eyeshield and an inner end pivotally connected to a first pivot point of said base, iii. a lower arm having an outer end pivotally connected to a lower point of said side portion of the eyeshield and an inner end pivotally connected to a second pivot point of said base, said second pivot point of said base being below said first pivot point of said base, iv. a low friction guide connected to a support point of said base rearward of said first and second pivot points thereof, below said first pivot point of said base, and above said second pivot point of said base, v. an elastic band having an upper segment engaging said low friction guide and an intermediate point of said upper arm, and a lower segment engaging said low friction guide and an intermediate point of said lower arm, the upper segment of said elastic band producing a first tensile force between said low friction guide and the intermediate point of said upper arm, the lower segment of said elastic band producing a second tensile force between said low friction guide and the intermediate point of said lower arm, portions of said elastic band moving around said low friction guide to the lower segment of said elastic band as the eyeshield is raised from a lower position of use to an upper position of non-use, portions of said elastic band moving around said low friction guide to the upper segment of said elastic band as the eyeshield is lowered from an upper position to said lower position, the first and second tensile forces being balanced by the movement of the portions of said elastic band around said low friction guide as the eyeshield moves from one of the lower and upper positions through a bistable point to the other of the lower and upper positions.

20. The eye protection device as claimed in claim 19 wherein said low friction guide is a bushing.

21. The eye protection device as claimed in claim 19 wherein said elastic band is a closed loop rubber band.

22. The eye protection device as claimed in claim 19 wherein as the eyeshield is raised, the upper segment of said elastic band moves away from the first pivot point of said base thereby increasing a component of the first tensile force tending to raise the eyeshield and the lower segment of the elastic band moves toward the second pivot point of the base thereby decreasing a component of the second tensile force tending to lower the eyeshield, and wherein as the eyeshield is lowered the upper segment of said elastic band moves toward the first pivot point of said base thereby decreasing a component of the first tensile force tending to raise the eyeshield and the lower segment of said elastic band moves away from the second pivot point of said base thereby increasing a component of the second tensile force tending to lower the eyeshield.

23. An eye protection device comprising an eyeshield pivotally connectable to a headgear by a pair of bistable tensioning pivotal mechanisms to position said eyeshield to an eye protection position of use and to a position of non-use away from the eyes of a wearer, each said mechanisms having a pair of pivotal arms pivotally connected at one end to a support base which is attachable to said headgear, each arm of said pair of pivotal arms having a free end pivotally connected to said eyeshield, spring biasing means secured to each said arm at a predetermined location with respect to a respective one of said first and second pivot connections, said spring biasing means exerting a pulling force in opposed directions to displace said arms in tandem between said position of use and non-use, abutment means associated with said pair of pivotal arms to arrest said arms at said position of use and position of non-use, said support base being adjustably secured to said headgear by a position adjusting mechanism whereby to cause relative displacement of said eyeshield with respect to a frontal position of said headgear.

24. An eye protection device as claimed in claim 17 wherein said position adjusting mechanism comprises a mounting plate secured to said headgear, said mounting plate having projecting abutment means extending through a slot in said support base to permit limited longitudinal displacement of said support base, and adjustment means to cause said displacement of said support base.

25. An eye protection device as claimed in claim 18 wherein said adjustment means is comprises by a threaded shaft secured at one end to said support base, said shaft extending through a stationary housing secured to said headgear and disposed in threaded engagement with a finger-actuable adjusting wheel arrested in said housing and partly accessible exteriorly of said housing.

26. A method of providing eye protection for a wearer of headgear comprising the steps of:
   (a) providing an attachable eyeshield with a bistable tensioning pivoting mechanism including pivotal arms having free ends connected to a support base in which the eyeshield alternatively has:
      1) an eye-protecting position; and
      2) a non-use position away from a user's line-of-sight; and
   (b) selectively mounting one of a plurality of different-strength, tensional elastic bands about free ends of the pivotal arms connected to said support base for providing a biasing force between alternate positions of use and non-use of said eyeshield.

27. The method of claim 26 including the step of providing the headgear in the form of a sweatband.

28. The method as claimed in claim 26 in which said bistable tensioning pivoting mechanism and pivotal arms are arranged to provide maximum force during the positions of use and non-use of said eyeshield.

29. An eye protection device comprising an eyeshield pivotally connectable to a headgear by a pair of bistable tensioning pivotal mechanisms to position said eyeshield to an eye protection position of use and to a position of non-use away from the eyes of a wearer, each said mechanism having a pivotal arm pivotally connected at one end to a support base which is attachable to said headgear, said pivotal arm having a free end connected to said eyeshield, said pivotal arm further having a first band engaging guide means secured at a predetermined location with respect to a pivot connection which secures said arm to said support base, said arm being displaceable on an arc about said pivot connection, a second band engaging guide means secured to said support base at a predetermined location with respect to said pivot connection, a stretchable elastic band formed as a loop and disposed in tension about and between both said band engaging guide means to exert a pulling force in opposed directions to displace said arms in tandem between said position of use and non-use, and abutment means to arrest said arm at said position of use and position of non-use.

30. An eye protection device as claimed in claim 29 wherein said abutment means is comprised of a first and second abutment element secured to said support base for abuttingly engaging arresting edge portions of said arm.

31. An eye protection device as claimed in claim 30 wherein said elastic band is removably connected about said band engaging means for replaceable connection thereto.

32. An eye protection device as claimed in claim 31 wherein said elastic band has a predetermined tensile strength, said band being interchangeable with other bands of different tensile strength to vary the strength of said pulling force.

33. An eye protection device as claimed in claim 29 wherein said arresting edge portions of said arm comprise a lower edge formation of said arm, and an upper edge formation of said arm, said upper edge formation of said arm being in abutting relationship with said first abutment element and arresting said arm at said position of non-use while said lower edge formation of said arm is in abutting relationship with said second abutment element and arrest said arm at said position of use.

34. An eye protection device as claimed in claim 31 wherein said pivotal arm is pivotally connected to said support base by a pivot connection, said pivot connection being offset from a straight axis passing through said first and second band engaging guide means.

35. An eye protection device as claimed in claim 34 wherein both said band engaging guide means are each constituted by an arcuate convexly curved guide surface of a guide element.

36. An eye protection device as claimed in claim 35 wherein said guide element is a guide sheave having opposed transverse guide walls to form an arcuate guide channel for retaining a portion of said elastic band captive therein.

37. An eye protection device as claimed in claim 29 wherein said headgear is a sweatband, said support base being secured to a rigid insert element.

38. An eye protection device as claimed in claim 37 wherein said support base is adjustably secured to said rigid insert element by a position adjusting mechanism whereby to cause relative displacement of said eyeshield with a frontal portion of said headband.

39. An eye protection device as claimed in claim 38 wherein said position adjusting mechanism has a finger-actuable adjusting element to cause displacement of said support base along restraining guide means, and a threaded connector interconnecting said finger-actuable adjusting element and said support base.

40. An eye protection device as claimed in claim 29 wherein said support base is adjustably secured to said headgear by a position adjusting mechanism whereby to cause relative displacement of said eyeshield with respect to a frontal position of said headgear.

* * * * *